(12) United States Patent
Raviv et al.

(10) Patent No.: US 6,258,043 B1
(45) Date of Patent: Jul. 10, 2001

(54) EAR PROBE TIP

(76) Inventors: Gabriel Raviv, 1048 Woodlawn, Glenview, IL (US) 60025; Ron Rolfsen, 270 Island View La., Lake Barrington, IL (US) 60010; Robert Tarasewicz, 711 59$^{th}$ St., Lisle, IL (US) 60532

( * ) Notice: Subject to any disclaimer, the term of this patent is extended or adjusted under 35 U.S.C. 154(b) by 0 days.

(21) Appl. No.: 09/225,754

(22) Filed: Jan. 5, 1999

(51) Int. Cl.$^7$ .................................................. A61B 5/00
(52) U.S. Cl. ................................................. 600/559
(58) Field of Search .................................. 600/559

(56) References Cited

U.S. PATENT DOCUMENTS

| | | |
|---|---|---|
| D. 265,129 | 6/1982 | Leight . |
| 2,487,038 | 11/1949 | Baum . |
| 3,097,643 | 7/1963 | Santi . |
| 3,935,401 | 1/1976 | Shore et al. . |
| 3,949,735 | 4/1976 | Klar et al. . |
| 4,055,233 | 10/1977 | Huntress . |
| 4,057,051 | 11/1977 | Kerouac . |
| 4,122,841 | 10/1978 | Rock et al. . |
| 4,374,527 | 2/1983 | Kemp . |
| 4,540,063 | 9/1985 | Ochi et al. . |
| 4,896,380 | 1/1990 | Kamitani . |
| 5,357,576 | * 10/1994 | Arndt .................................. 381/328 |

OTHER PUBLICATIONS

Short Course, Overviews and tutorials on important clinical and professional topics, "Otoacoustic Emissions", Theodore J. Glattke and Sharon G. Kujawa, Department of Speed and Hearing Sciences, University of Arizona, Tucson, Nov. 1991, pp. 29–37.

"ABR 20 Years Later: Answers to 5 Commom Clinical Questions", James W. Hall, III, *The Hearing Journal*, Feb. 1992, vol. 45, No. 2, pp. 22–25.

* cited by examiner

*Primary Examiner*—Max Hindenburg
*Assistant Examiner*—Pamela L Wingood
(74) *Attorney, Agent, or Firm*—Marshall, O'Toole, Gerstein, Murray & Borun

(57) ABSTRACT

An improved ear probe tip for the end of a probe which can be inserted into an ear canal. The ear probe tip comprises a body portion having an inner surface, an outer surface, a first end and a second end. The body portion inner surface defines a passage that extends the entire length of the body portion. The ear probe tip also has a plurality of flexible annular flanges disposed at spaced intervals on the outer surface of the body portion.

17 Claims, 4 Drawing Sheets

EAR PROBE TIP

FIELD OF THE INVENTION

The present invention relates to ear probe tips, and more particularly to removable ear probe tips that provide for protection of the ear canal and provide for an enhanced self-adjusting acoustical seal between the ear probe tip and the ear canal.

BACKGROUND OF THE INVENTION

Ear probe tips of various types are well known in the art. Such devices are typically used in combination with testing equipment for clinical evaluation of hearing loss and/or ear disease. For example, there are procedures for evaluating hearing loss, ear disease or other ear disorders which are known as otoacoustic emissions (OAE) testing and auditory brain-stem response (ABR)testing. Such tests, which rely on acoustical measurements made within the patient's ear canal, include the step of closing off the ear canal with a probe or a removable probe tip. The probe tip may form a seal between the ear canal and the probe tip so that the transmission and receipt of acoustical signals within the closed cavity may be controlled. Several other hearing tests use probes with tips.

However, previous ear probe tips have some inherent disadvantages. One of the disadvantages with prior art tips is that they require an acoustical sound passage or else the test procedure will produce unreliable results. Requiring the tip to include an acoustical sound passage is undesirable because this adds to the cost of manufacturing each tip.

Another disadvantage is that they are not well adapted to different ears. Persons' ears differ in size and shape and have outer ear canals of varying configurations. As a result, great difficulties have been encountered with prior ear probe tips because in most situations, the tip exerts too great a pressure on the ear canal, fails to provide a good acoustic seal between it and the ear canal, or does not prevent the hard inflexible probe end from extending past the tip thereby increasing the risk of resulting damage to the person's ear.

The present invention overcomes these and other problems inherent in existing ear probe tips. The present invention provides an ear probe tip that fits around the probe. A feature of an embodiment of the ear probe tip is that flexible flanges form a substantial acoustic seal between the probe and the outer ear canal for a wide range of ear canal size, thereby permitting ear testing to be done quickly and conveniently without critical adjustments of the probe or of the probe tip. This is of particular value in the case of children or other patients who may have a short attention span or an inability to cooperate in the test procedures. Further, in one embodiment, the probe tip is designed so that it can receive the probe, whereby the probe tip can be positioned fully over the probe while still allowing the probe tip's end to slightly extend past the end of the probe. This configuration does not require each probe tip to comprise an acoustical channel, thereby minimizing the cost to manufacture each probe tip. Further, since the cost is minimized, the probe tip can be disposed of after one use thereby eliminating the need for probe cleaning and providing optimal infection control.

The principal object of the present invention is to provide an improved ear probe tip for use with testing apparatus for hearing loss or other ear problems.

Another object of the present invention is to provide a novel ear probe tip of more efficient form for providing better sealing between the probe tip and a wide range of ear canal size.

Still another object of the present invention is to provide a novel ear probe tip that protects the ear from the probe when the probe is inserted into the ear canal.

A further object of the present invention is to provide a novel ear probe tip that will provide for enhanced retention of the ear probe tip once the ear probe tip is received by the ear canal.

A further object of the present invention is to provide a novel removable ear probe tip that secures easily to a probe end.

A further object of the present invention is to provide a novel ear probe tip which is simple in design and inexpensive to construct, and is durable and rugged in structure.

Still further objects and advantages will become apparent from a consideration of the ensuing description and drawings of the invention.

These and other objects are achieved by an ear probe tip of the present invention. In one form of the invention, an ear probe tip is provided which comprises a body portion having an inner surface, an outer surface, a first end and a second end. The body portion inner surface defines a passage that extends the entire length of the body portion. The ear probe tip also has a plurality of flexible annular flanges disposed at spaced intervals on the outer surface of the body portion.

DETAILED DESCRIPTION

Figure 1:
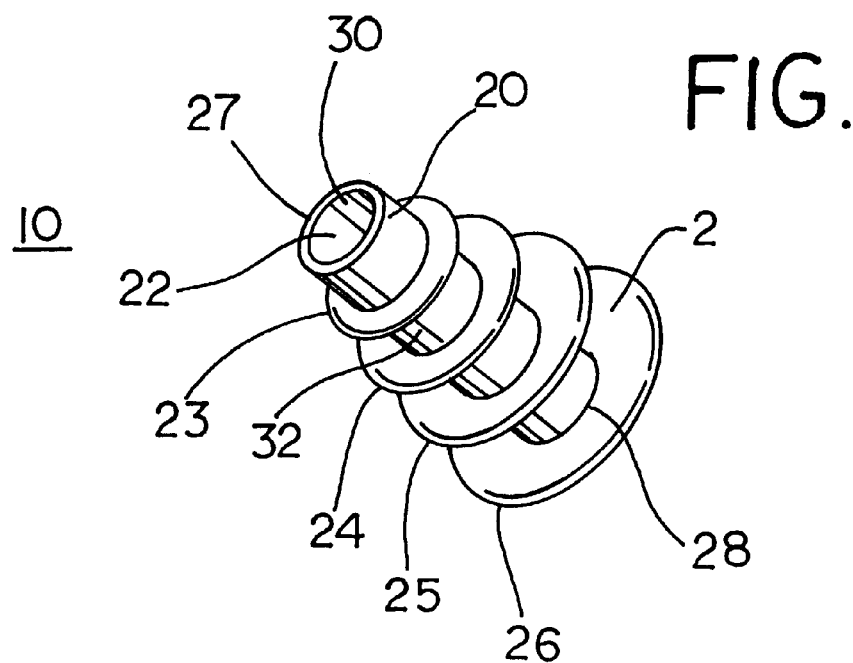
FIG. 1 is a perspective view of one embodiment of the ear probe tip of the present invention.
Figure 2:
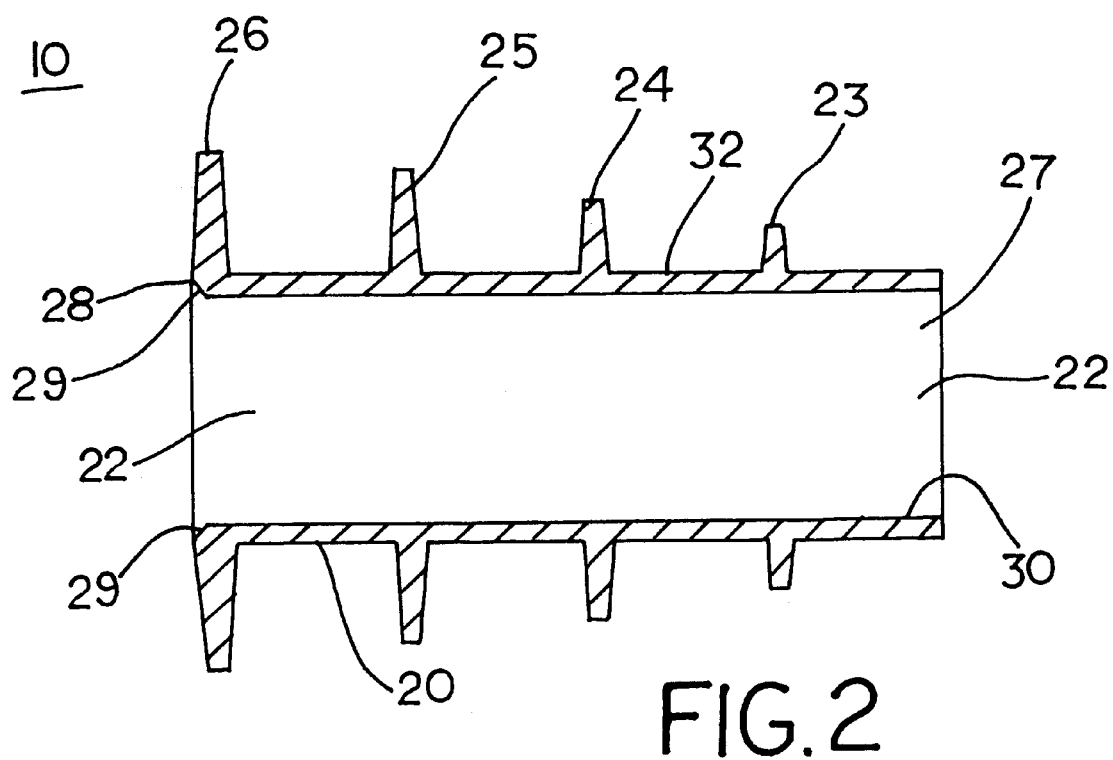
FIG. 2 is a cross sectional view of the ear probe tip of FIG. 1.
Figure 3:
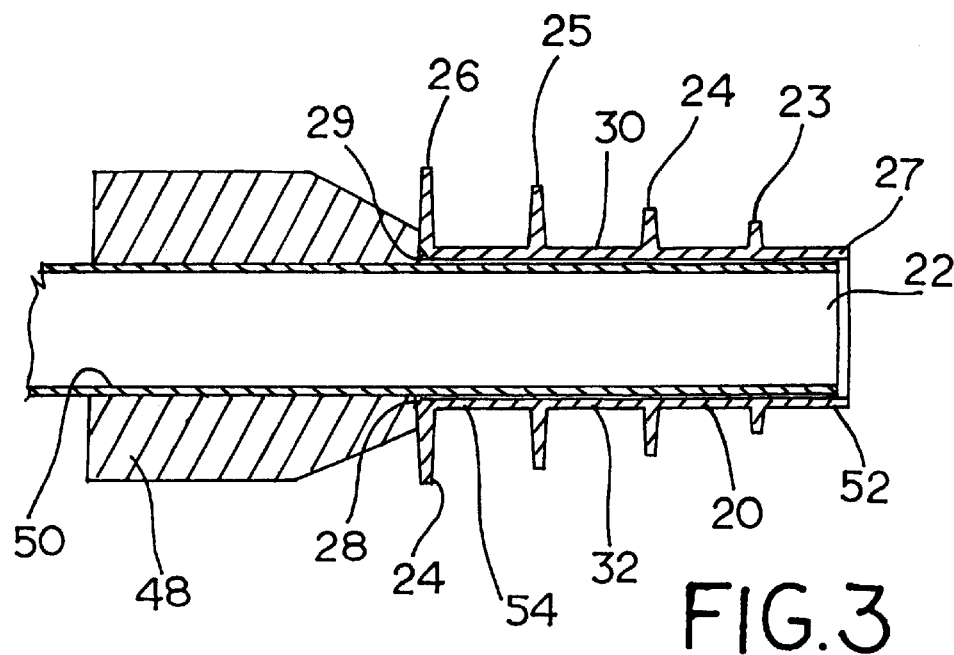
FIG. 3 is a view of the ear probe tip of FIG. 1 shown in place on an ear probe end.

FIG. 1 is a perspective view of one embodiment of the ear probe tip 10 constructed in accordance with the present invention. In FIG. 1, the ear probe tip 10 comprises a body portion 20 and a plurality of flexible annular flanges 23, 24, 25, 26. The body portion 20 may be tube shaped and hollow (as shown in FIG. 1) and have a passage 22, a first end 27 and a second end 28. In one embodiment, the passage 22 extends the entire length of and runs axially through the body portion 20. The second end 28 of the body portion 20 has a chamfer 29 (see FIG. 2). The chamfer 29 may, for example, be cut at a 45 degree angle from the passage 22 longitudinal centerline. The chamfer 29 facilitates the insertion of the probe 50 into the tip 10. Body portion 20 may, for example, have an inner diameter of 0.134 inches and an outer diameter of 0.154 inches or any other diameters that provide for proper operation of the tip 10 for use in a specific application. Passage 22 may, in an alternate embodiment, run the entire length of the body portion 20 at a distance offset the body portion 20 axis. A plurality of flexible annular flanges 23, 24, 25, 26 are disposed on the exterior of body portion 20. As best seen in FIG. 2 and 3, in one embodiment the flanges 23, 24, 25, 26 are attached substantially perpendicular to the body portion 20. As an example, the flange 23 proximal the first end 27 may have an outer diameter of 0.200 inches, so as to fit securely and sealably into the internal portion of the ear canal. Also, as measured from the flange 23 longitudinal centerline, the flange 23 may be offset from the first aperture 0.096 inches or any other distance that is necessary for proper performance of the tip 10. In the illustrated embodiment (FIG. 1, 2, 3), each flange 23, 24, 25, 26 that is distal the flange 23, 24, 25, 26 has a progressively greater outer diameter. Accordingly, flange 24, 25, 26 may have outer diameters of 0.238, 0.275 and 0.312 inches, respectively, to sealably and securely fit into the ear canal. Each flange 23, 24, 25, 26 may be 0.112 inches apart from the flange 23, 24, 25, 26 adjacent to it as measured along the longitudinal centerline of each flange 23, 24, 25, 26 or the flange 23, 24, 25, 26 longitudinal centerline spacing can be any other distance necessary for proper performance of the tip 10. As shown in FIGS. 1, 2 and 3, in the illustrated embodiment the tip 10 has four flanges 23, 24, 25, 26. However, alternate embodiments can have any number of flanges 23, 24, 25, 26 that provide for proper operation of the tip 10. Also, an alternate embodiment may have no flanges 23, 24, 25, 26. In this embodiment, the body portion 20 provides the necessary seal with the ear canal. Further, alternate embodiments may provide flanges 23, 24, 25, 26 of varying thickness and shapes. The cross-sectional shape of the flanges 23, 24, 25, 26, for example, may have virtually any shape such as a circle, triangle, square, etc. Flanges 23, 24, 25, 26 may taper as they extend outwardly away from the body portion 20.

To ensure a comfortable fit and to provide the necessary seal, in one embodiment the tip 10 may be made of alpha gary pvc 3019-40/45 or some other suitable soft flexible material such as latex or silicone. This type of material will also prevent the patient's ear from being scratched or otherwise injured by the tip 10. The material can also be transparent to allow for easy detection of vernix, cerumen, or wax build-up in the tip 10.

FIG. 3 illustrates one embodiment of the tip 10 in place over a probe 50 and positioned adjacent a probe base 48. The probe base 48 and probe 50 are components of an existing hearing testing apparatus. When the tip 10 is fully positioned over a probe end 52 (as in FIG. 3), the tip 10 extends past the end of the probe end 52, thereby preventing the probe end 52 from coming into contact with the ear. This further ensures that the patient's ear will not be scratched or otherwise injured by the rigid probe end 52. Also, as can best be seen in FIG. 3, in a preferred embodiment the passage 22 should be adapted and sized to accept the probe end 52 so that substantially the entire length of the passage 22 can receive the probe end 52 thereby eliminating the need for the passage 22 to form an acoustic channel. This design feature considerably reduces the manufacturing costs of the tip 10. Further, when fully in place over the probe end 52, the second end 28 may rest substantially flush against the probe base 48. This arrangement further ensures that the tip 10 does not move out of proper operating position with respect to the probe end 52 when the tip 10 is inserted into the ear canal.

Figure 4:
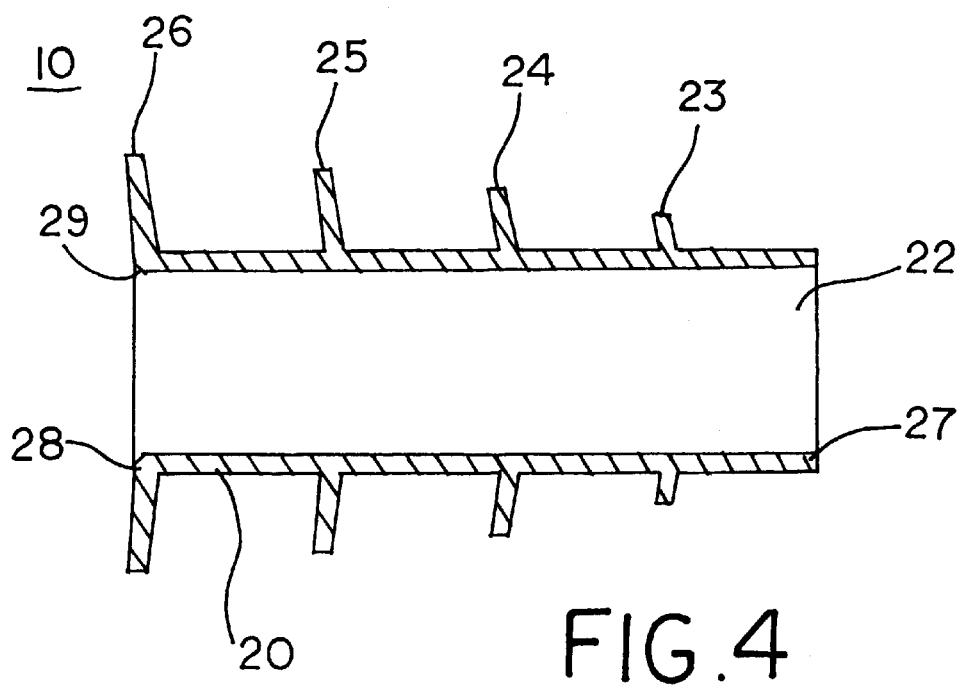
FIG. 4 is a cross sectional view of an alternate embodiment of the ear probe tip of FIG. 1.

FIG. 4 shows a cross sectional view of an alternate embodiment of the tip 10 of the present invention. The flanges 23, 24, 25, 26 may be attached to the body portion 20 so that the flanges 23, 24, 25, 26 extend outwardly and rearwardly toward second end 28. Depending on the con- figuration of the ear canal that the tip 10 is inserted into, this flange 23, 24, 25, 26 arrangement may further prevent the tip 10 from slipping out of the ear canal. This flange 23, 24, 25, 26 arrangement may also provide an enhanced acoustical seal between the ear canal and the tip 10.

Figure 5:
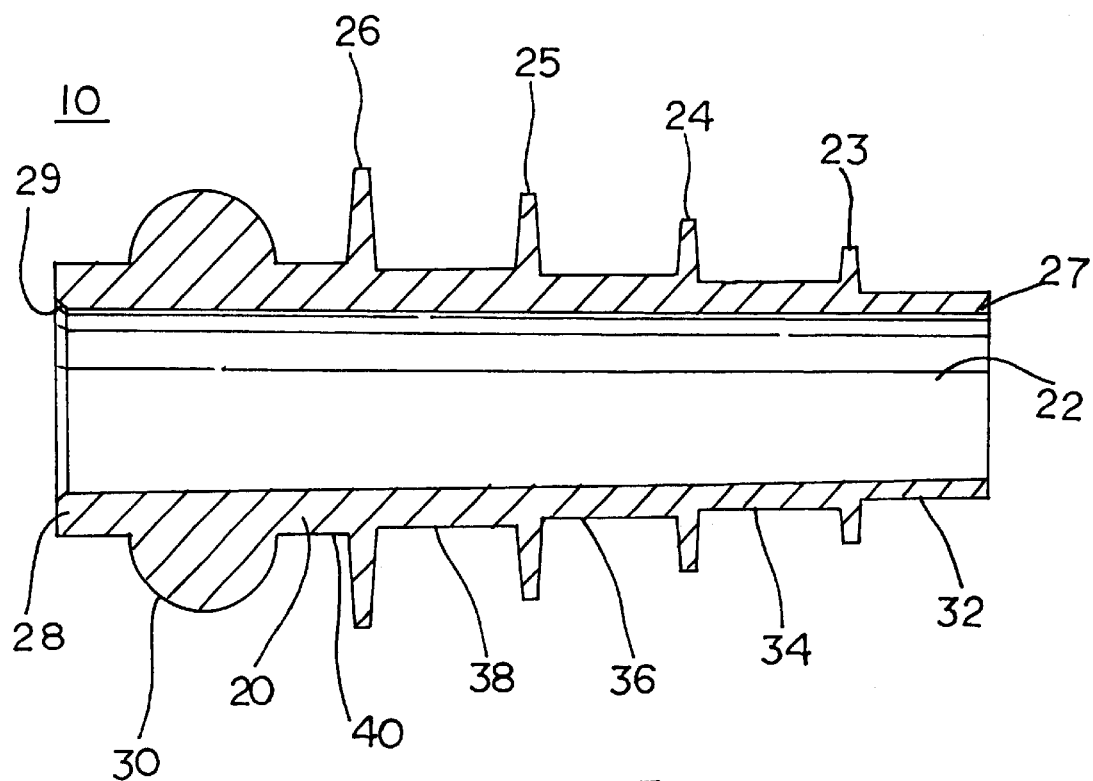
FIG. 5 is a cross sectional view of another alternate embodiment of the ear probe tip of FIG. 1.

FIG. 5 shows a cross sectional view of another alternate embodiment of the tip 10 of the present invention. As shown in the example of FIG. 5, body portion sections 32, 34, 36, 38, 40 may be of varying outer diameters, e.g., 0.140, 0.155, 0.165, 0.175, 0.185 inches, respectively. Depending on the configuration of the ear canal that the tip 10 is inserted into, varied outer diameters of body portion sections 32, 34, 36, 38, 40 may further provide an enhanced acoustical seal between the ear canal and the tip 10. This body portion section 32, 34, 36, 38, 40 configuration may further prevent the tip 10 from slipping out of the ear canal.

Also, a ring 30 may be disposed on the body portion 20 between the second end 28 and the flange 26. The ring 30 may be grasped by hand to facilitate positioning the ear probe tip 10 over the probe 50. Further, it is desirable to grasp the ring 30 instead of the flanges 23, 24, 25, 26, because if the flanges 23, 24, 25, 26 are damaged the ear probe tip 10 will not operate properly. Accordingly, the ring 30 may be located 0.100 inches from the second end 28 as measured from the ring center line. The ring 30 may have a radius of 0.050 inches or whatever other radius necessary for proper performance of the ear probe tip 10. The ring 30 cross sectional area may be in the shape of a half circle or any other shape necessary for proper performance of the ear probe tip 10. The ring 30 may be continuous or non-continuous around the outer surface of the body portion 20.

Further, in an alternate embodiment, body portion 20 inner surface 31 diameter may increase in size along the length of the body portion 20 toward the second end 28. Body portion inner surface 31 diameter at the first end 27 and the second end 28 may be, for example, 0.110 and 0.127 inches, respectively. This configuration may provide for enhanced positioning of the ear probe tip 10 over the probe 10.

Figure 6:
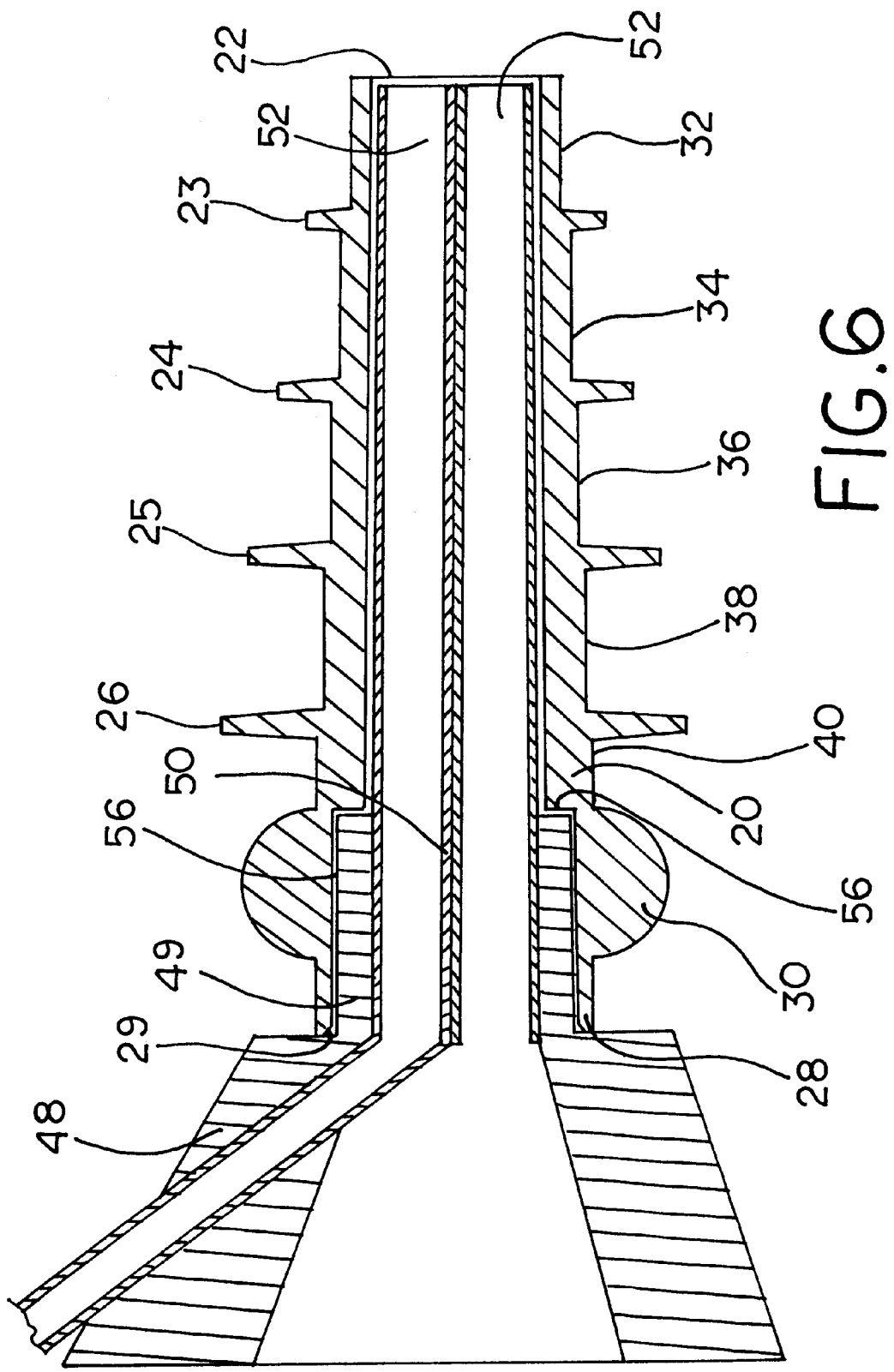
FIG. 6 is a cross sectional view of another alternate embodiment of the ear probe tip of FIG. 1 shown in place on an ear probe end.

FIG. 6 shows a cross sectional view of still another alternate embodiment of the tip 10 of the present invention shown in place on an ear probe end. As illustrated in FIG. 6, body portion 20 inner surface 31 diameter may increase in size near the second end 28 so that it is sized to fit snugly over a probe base extension 49 when the tip 10 is fully in place over the probe end 52 and the second end 28 is substantially flush against probe base 48. This configuration may provide for enhanced positioning of the ear probe tip 10 over the probe end 52. As shown in FIG. 6, there may be more than one probe end 52 positioned adjacent each other that the tip 10 will fit over.

As shown in FIG. 6, body portion sections 32, 34, 36, 38, 40 may be of varying outer diameters, e.g., 0.140, 0.155, 0.165, 0.175, 0.185 inches, respectively. Depending on the configuration of the ear canal that the tip 10 is inserted into, varied outer diameters of body portion sections 32, 34, 36, 38, 40 may further provide an enhanced acoustical seal between the ear canal and the tip 10. This body portion section 32, 34, 36, 38, 40 configuration may further prevent the tip 10 from slipping out of the ear canal.

However, alternate embodiments can have any number of flanges 23, 24, 25, 26 that provide for proper operation of the tip 10. Also, an alternate embodiment may have no flanges 23, 24, 25, 26. In this embodiment, the body portion 20 provides the necessary seal with the ear canal. Further, alternate embodiments may provide flanges 23, 24, 25, 26 of varying thickness and shapes. The cross-sectional shape of the flanges 23, 24, 25, 26, for example, may have virtually any shape such as a circle, triangle, square, etc. Flanges 23, 24, 25, 26 may taper as they extend outwardly away from the body portion 20.

Also, a ring 30 may be disposed on the body portion end 21 (or body portion 20) between the second end 28 and the flange 26. The ring 30 may be grasped by hand to facilitate positioning the ear probe tip 10 over the probe end 52. Further, it is desirable to grasp the ring 30 instead of the flanges 23, 24, 25, 26, because if the flanges 23, 24, 25, 26 are damaged the ear probe tip 10 may not operate properly. Accordingly, the ring 30 may be located 0.100 inches from the second end 28 as measured from the ring center line. The ring 30 may have a radius of 0.050 inches or whatever other radius necessary for proper performance of the ear probe tip 10. The ring 30 cross sectional area may be in the shape of a half circle or any other shape necessary for proper performance of the ear probe tip 10. The ring 30 may be continuous or non-continuous around the outer surface of the body portion 20.

Referring back to FIG. 3, when using the tip 10, the tip 10 (or if present the ring 30) is grasped by hand and the tip 10 is pushed over the probe end 52. The tip 10 is positioned over the probe end 52 so that tip 10 extends past the probe end 52. When the probe end 52 with the tip 10 securely in place is inserted into the patient's ear canal, the flanges 23, 24, 25, 26 bend and flex where necessary so that the plurality of flanges 23, 24, 25, 26 form a self-adjusting acoustic seal between the tip 10 and the outer ear canal of the user. The flanges 23, 24, 25, 26 are designed to ensure that the radial extent of the flanges 23, 24, 25, 26 provides the necessary contact area between each flange 23, 24, 25, 26 and the ear canal to create the required seal. The seal substantially prevents ambient noise from entering the ear canal. The flanges 23, 24, 25, 26 also provide for the tip 10 to remain securely positioned in the ear canal, thereby minimizing the amount of time necessary to perform the procedure. This is especially desirable in the case of children and certain other patients who may have a short attention span or an inability to cooperate during the test procedures. Further, body portion 20 is designed to prevent appreciable compression in the longitudinal direction in order to prevent the probe end 52 from exiting the first aperture 27, extending past the tip 10 and scratching or otherwise injuring the ear. Also note that it is desirable for the flange 23 to be offset from the first end 27 because the body portion 20 may by itself provide a proper seal when it is inserted into an ear canal that is substantially the same dimension as the outer diameter of the body portion 20. Therefore, by having the flange 23 offset from the first end 27, the tip 10 can adapt to fit a larger variety of ear canal sizes. Provided the tip 10 is secured in the ear canal, whether by at least one flange 23, 24, 25, 26, or by just the body portion 20 and the seal is formed, the appropriate testing can commence.

For example, one form of clinical test that requires a probe be inserted into a patient's ear canal is OAE. During OAE testing, two signals are delivered to the probe 50 and pass through the probe 50 past the first end 27 and into the patient's ear. The tones then travel through the patient's ear canal until they come into the middle ear where they are partially absorbed and partially result in a return difference signal propagated back toward the first end 27 whereby they are channeled back into the passage 22 because of the seal created by the flanges 23, 24, 25, 26 and the users ear canal. The signal channeled back into the passage 22 continues into the probe 50 and is detected by a low noise microphone which delivers a signal to the OAE testing device being used during this specific testing procedure. The signal is subsequently analyzed to determine the condition of the patient's ear.

Specific embodiments of novel methods and apparatus for construction of novel ear probe tips according to the present invention have been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention any and all modifications, variations, or equivalents that fall within the true spirit and scope of the basic underlying principles disclosed and claimed herein.

We claim:

1. An ear probe tip for the end of a probe which can be inserted into an ear canal, said ear probe tip comprising:
    a body portion having an inner surface, an outer surface, a first end and a second end, wherein the inner surface diameter of the body portion increases in size along the length of the body portion toward the second end; and
    a ring located on the outer surface of the body portion proximal the second end.

2. The ear probe tip of claim 1 further comprising at least one flexible annular flange disposed on the outer surface of the body portion at a distance from the first end.

3. An ear probe tip for the end of a probe, which can be inserted into an ear canal, said ear probe tip comprising:
    a body portion having an inner surface, an outer surface, a first end and a second end, the inner surface defining a passage that extends the entire length of the body portion,
    wherein the passage can receive the probe end and wherein the inner surface diameter of the body portion increases in size along a length of the body portion toward the second end; and
    at least one flexible annular flange disposed on the outer surface of the body portion.

4. The ear probe tip of claim 3, wherein the at least one flange is located proximate the first end.

5. The ear probe tip of claim 3, wherein the at least one flange is disposed on the body portion at a distance from the first end.

6. The ear probe tip of claim 3, wherein the body portion outer surface diameter increases along the length of the body portion toward the second end.

7. The ear probe tip of claim 3, wherein the at least flange is disposed on the body portion at a backward angle toward the second end.

8. The ear probe tip of claim 3, further comprising means for pushing the ear probe tip onto the probe.

9. The ear probe tip of claim 8, wherein the means for pushing the ear probe tip onto the probe is a ring located on the body portion proximate the second end.

10. An ear probe tip for the end of a probe, which can be inserted in to an ear canal, said ear probe tip comprising:
    a body portion having an inner surface, an outer surface, a first end and a second end, the inner surface defining a passage that extends the entire length of the body portion,
    wherein the passage can receive the probe end and wherein the inner surface diameter of the body portion increases in size along the length of the body portion toward the second end and communicates with a cavity located proximate the second end; and
    at least one flexible annular flange disposed on the outer surface of the body portion.

11. The ear probe tip of claim 10, wherein the at least one flange is located proximate the first end.

12. The ear probe tip of claim 10, wherein the at least one flange is disposed on the body portion at a distance from the first end.

13. The ear probe tip of claim 10, wherein the body portion outer surface diameter increases along the length of the body portion toward the second end.

14. The ear probe tip of claim 10, wherein the at least flange is disposed on the body portion at a backward angle toward the second end.

15. The ear probe tip of claim 10, further comprising means for pushing the ear probe tip onto the probe.

16. The ear probe tip of claim 10, wherein the means for pushing the ear probe tip onto the probe is a ring located on the body portion proximate the second end.

17. An ear probe tip for the end of a probe, which can be inserted into an ear canal, said ear probe tip comprising:

a body portion having an inner surface, an outer surface, a first end and a second end, wherein the outer surface has a diameter which increases along the antecedent length of the body portion toward the second end; and a passage defined by the inner surface that extends substantially the length of the body portion wherein the passage can receive the probe end and wherein the inner surface diameter of the body portion increases in size near the second end.

\* \* \* \* \*